United States Patent [19]

Gainer

[11] 3,975,519
[45] Aug. 17, 1976

[54] METHOD FOR INCREASING THE OXYGEN PARTIAL PRESSURE IN THE BLOODSTREAM OF MAMMALS

[75] Inventor: John L. Gainer, Charlottesville, Va.

[73] Assignee: University of Virginia, Charlottesville, Va.

[22] Filed: June 9, 1975

[21] Appl. No.: 584,946

[52] U.S. Cl. ............................ 424/180; 424/318; 424/319; 424/325; 424/343
[51] Int. Cl.² ................ A61K 31/70; A61K 31/20; A61K 31/195; A61K 31/13
[58] Field of Search ........... 424/343, 180, 318, 325, 424/319

[56] References Cited
UNITED STATES PATENTS 3,788,468   1/1974   Gainer ............................ 424/318
3,853,993   12/1974  Gainer ............................ 424/180

OTHER PUBLICATIONS

Benk – Chem. Abst. vol. 67 (1967) p. 2253s. –

Primary Examiner—Sam Rosen
Attorney, Agent, or Firm—Oblon, Fisher, Spivak, McClelland & Maier

[57] ABSTRACT

A method for increasing the partial pressure of $O_2$ in blood in a mammal, which comprises administering to said mammal an effective dose of a water soluble carotenoid, whereby the $O_2$ partial pressure in the bloodstream of said mammal is increased.

5 Claims, No Drawings

METHOD FOR INCREASING THE OXYGEN PARTIAL PRESSURE IN THE BLOODSTREAM OF MAMMALS

BACKGROUND OF THE INVENTION

1. Field of the Invention

This invention relates to a novel technique to increase oxygen partial pressure in the blood stream of mammals.

2. Description of the Prior Art

In applicants' prior applications, now U.S. Pat. Nos. 3,853,993 and 3,788,468, applicant disclosed that certain water-soluble carotenoids has been observed to possess quite unique properties. In particular, these water-soluble carotenoids have been found to increase the diffusivity of oxygen through aqueous media. Applicant theorized that this phenomenon might be applied to effect desirable biological effects. In particular, applicant theorized that if oxygen diffusivity in aqueous media could be enhanced, that this effect could be applied to increase the diffusivity of oxygen in blood. Applicant theorized further that by increasing the diffusivity of oxygen in the blood, atherosclerosis, which has long been theorized to be a disease resulting from local hypoxia of the vascular walls, could be successfully treated. This theory was applied to certain test animals, and, to the satisfaction of the inventors, the theory was proven to be correct, and in fact, a seemingly successful treatment of atherosclerosis was obtained.

It has been known that it would be desirable to increase the partial pressure of $O_2$ in the bloodstream for the treatment of a variety of disorders. This treatment is known as oxygen therapy, and is currently carried out by placing the subject in an oxygen tent. This treatment is of particular importance in respiratory diseases such as asthma, pulmonary emphysema and cistic fibrosis, but is also frequently used in intensive care units for treating many other diseases such as myocardial infarctions, for example.

The uptake of oxygen by the blood in the lungs is assumed by most people to be perfusion-limited, rather than diffusion-limited. This means that it is the rate of blood flow through the capillaries in the lungs which determines how much oxygen is taken up by the blood (See: T. C. Ruch and D. D. Patton, "Physiology and Biophysics", W. B. Saunders Do., Philadelphia, 1965, p. 736; J. B. West, "Respiratory Physiology – the Essentials", Williams and Wilkins, Baltimore, 1974, p. 26; B. A. Schottelius and D. D. Schottelius, "Textbook of Physiology", 17th ed., C. V. Mosly Co., St. Louis, 1973, p. 331). Thus, since it is difficult to increase the blood flow through the capillaries to the lungs, it is common to put people requiring increased oxygenation of their blood in oxygen tents where the partial pressure of oxygen varies from 40 – 60% (rather than the 21% in normal air). The invention described of using carotenoid to increase the partial pressure of oxygen in the blood is an alternative to using the oxygen tent. Although the principle through which it works may be due to diffusion increases, this is in contrast to the currently-accepted theory of perfusion limitation mentioned above. So it is possible that the effect of carotenoid of increasing the partial pressure of oxygen in the blood is not due to increasing the diffusivity of oxygen.

Applicant has now continued to study the biological properties of this most unusual class of compounds, with the result that a new biological property has been discovered which is the subject matter of this application.

SUMMARY OF THE INVENTION

It has now been found that water-soluble carotenoid compounds, such as crocetin and crocin, can be used effectively to increase the $O_2$ partial pressure of the blood in mammals.

DETAILED DESCRIPTION OF THE PREFERRED EMBODIMENTS

In applicants' prior patents, it was discovered that the water-soluble carotenoids are effective for increasing the diffusivity of oxygen in aqueous media, including blood. What is particularly surprising in this invention, however, is the discovery that the water-soluble carotenoids also have the effect of causing a higher rate of oxygen transfer from the lung membranes into the bloodstream. Whereas the prior patents disclosed that the carotenoids could increase the rate of oxygen transfer within the aqueous media, the present invention is the unexpected enhanced rate of transfer of the oxygen from the gaseous state through lung tissue and into the bloodstream.

This phenomena of increased oxygen partial pressure will find a very wide range of medical applications. For instance, this technique can be used to provide relief in the treatment of cystic fibrosis, asthma, emphysema, and in intensive care units where oxygen tents are currently used. Use of oxygen therapy with increased oxygen environments is a standard medical practice.

For instance, pulmonary emphysema is a lung disease characterized by enlargement, overdistention and destructive changes in the air spaces distal to the terminal nonrespiratory bronchioles. It varies widely in extent, and various forms have been differentiated pathologically. In all forms, the pathological changes which occur result in a reduction in the area of the alveolar membrane available for gas exchange. This reduction in the area available for gas exchange results in defective oxygen uptake by the bloodstream. Decreased values of oxygen tension in the arteriol blood ($P_O$ ) are frequent, especially in the advanced stages of the disease.

Treatment with water-soluble carotenoids, however, can alleviate the problem associated with decreased oxygen levels and thereby counteract the effects of the pulmonary emphysema.

The carotenoids useful for this purpose are those of the form:

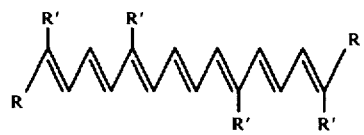

wherein each R may represent a hydrophilic group and each R' represents hydrogen or methyl. Suitable hydrophilic groups include the carboxyl groups or the ester groups of the form COOR'' wherein R'' represents a soluble sugar group, such as $C_{12}H_{21}O_{10}$, an alkanol group, such as —$CH_2$—OH, —$CH_2$—$CH_2$—OH, or —$CH_2$—$CH_2$—$CH_2$—OH, or a carboxy substituted lower alkyl, such as —$CH_2$—COOH, —$CH_2$—CH- $_2$—COOH or —CH$_2$—CH$_2$—CH$_2$—COOH, or each R and R' may represent a lower alkanol group, such as —CH$_2$—OH, —CH$_2$—CH$_2$—OH, or —CH$_2$—CH$_2$—CH$_2$—OH, a hydroxy group, or an amine group of the form —NH or NR''' wherein R''' is a lower alkyl, lower alkanol or carboxy substituted lower alkyl, or a carboxy substituted lower alkyl, such as —CH$_2$—CH$_2$—OH, —CH$_2$—OH, or —CH$_2$—CH$_2$—CH$_2$—OH.

Most preferred are crocetin, also known as 8,8'-diapo-8,8'-carotenoic acid, or crocin, also known as digentiobiosyl 8,8'-diapo-8,8'-carotenedioate.

The water soluble carotenoids have been found to be effective in increasing the partial pressure of oxygen in the bloodstream when applied by intraveneous injection into the bloodstream both when dissolved in saline or in blood serum. It could also be taken orally alone or dissolved in glycols, glycerine, aqueous solutions, or other pharmaceutical carriers. The recommended dosage of the carotenoid would be 0.001–1000 mg/kg/week.

The carotenoid can be used in an injectable form combined with vitamins, particularly Vitamin A, choline, glycerophosphoric acid, glycol, glycerine or gum tragacanth, etc.

The animal or human is treated with from 0.0003 mg to 200 mg and preferably 0.001 to 100 mg of active ingredient per kg of body weight each application, for a total weekly dose rate of 0.0015 to 1000 mg of active ingredient per kg of body weight/day, and preferably from 0.0003 to 1 mg/kg/day or 0.001 to 10 mg/kg/week.

The effectiveness of the water soluble carotenoids for increasing O$_2$ partial pressure has been indicated by tests with male rabbits of the New Zealand white variety, which is the standard test animal often used for blood experiments.

The normal O$_2$ partial pressure in the blood of humans is 100 mm Hg. In the case of a drop in this pressure, the water-soluble carotenoid of this invention is effective in restoring normal pressure in about 10 minutes to an hour.

Although the carotenoids have been identified herein as "water-soluble carotenoids", it should be understood that they also are soluble in hydrocarbons due to their long chain hydrocarbon structure.

Having generally described the invention, a more complete understanding can be obtained by reference to the following specific example, which is included for purposes of illustration only and is not intended to be limiting unless otherwise specified.

EXAMPLE 1

7 Male rabbits, weighing about 4 kilograms each, of the New Zealand white variety were used. The animals were anesthetized with sodium pentabarbital, a cannula inserted into the femoral artery, and blood samples withdrawn periodically and tested for oxygen content using an IL (Instrument Laboratories) Blood Gas Analyzer. After the resting period, about 10 ml of a solution containing crocetin dissolved in normal saline or in rabit serum was injected at a concentration of around 30 μg/ml of crocetin. Blood samples were again withdrawn and the oxygen contents measured. The results are shown in Table 1. In all cases, the partial pressure of oxygen in the blood increased significantly about 15–20 minutes after the crocetin-saline had been injected. The injections were done intraveneously in the ear vein. Thus, it appears that crocetin is aiding oxygenation of the blood.

TABLE 1

EFFECT OF CROCETIN INJECTIONS ON THE OXYGEN PARTIAL PRESSURE IN THE BLOOD OF A RABBIT FROM THE FEMORAL ARTERY

| Beginning level $P_{O_2}$ (mm Hg) | After crocetin $P_{O_2}$ (mm Hg) |
|---|---|
| 62 | 92 |
| 58 | 97 |
| 90 | 98 |
| 90 | 118 |
| 80 | 94 |
| 93 | 100 |
| 35 | 95 |

Having now fully described the invention, it will be apparent to one of ordinary skill in the art that many changes and modifications can be made thereto without departing from the spirit or scope of the invention as set forth herein.

What is claimed as new and intended to be convered by Letters Patent is:

1. A method for raising the oxygen partial pressure in the bloodstream which comprises administering to a mammal in need of such treatment an effective dose of a water-soluble carotenoid, whereby the oxygen partial pressure is increased.

2. The method of claim 1, wherein said water-soluble carotenoid has the formula:

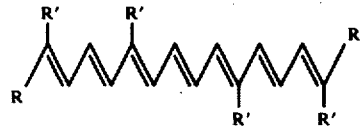

wherein each R is a hydrophilic group, and wherein each R' is hydrogen or methyl.

3. The method of claim 1, wherein said water-soluble carotenoid is crocin.

4. The method of claim 1, wherein said water-soluble carotenoid is crocetin.

5. The method of claim 1, wherein said water-soluble carotenoid is administered intraveneously at a dose rate of from 0.001 mg to 1000 mg active ingredient per kg of body weight per week.

* * * * *